United States Patent
Woods

(10) Patent No.: US 11,524,108 B2
(45) Date of Patent: Dec. 13, 2022

(54) CASSETTE ASSEMBLY FOR AMBULATORY DRUG PUMP

(71) Applicant: INFUSAID MEDICAL MFG, LLC, West Chester, PA (US)

(72) Inventor: Christopher D. Woods, West Chester, PA (US)

(73) Assignee: INFUSAID MEDICAL MFG, LLC, West Chester, PA (US)

( * ) Notice: Subject to any disclaimer, the term of this patent is extended or adjusted under 35 U.S.C. 154(b) by 0 days.

(21) Appl. No.: 17/764,563

(22) PCT Filed: Nov. 11, 2020

(86) PCT No.: PCT/US2020/059913
§ 371 (c)(1),
(2) Date: Mar. 29, 2022

(87) PCT Pub. No.: WO2021/096899
PCT Pub. Date: May 20, 2021

(65) Prior Publication Data
US 2022/0347379 A1  Nov. 3, 2022

Related U.S. Application Data

(60) Provisional application No. 62/934,142, filed on Nov. 12, 2019.

(51) Int. Cl.
*A61M 5/148* (2006.01)
*A61M 5/14* (2006.01)

(52) U.S. Cl.
CPC .......... *A61M 5/1413* (2013.01); *A61M 5/148* (2013.01); *A61M 2205/123* (2013.01)

(58) Field of Classification Search
CPC .............. A61M 5/142; A61M 5/14228; A61M 5/14232; A61M 2205/12; A61M 2205/123; A61J 1/10; A61J 1/1493; B65D 83/0094
See application file for complete search history.

(56) References Cited

U.S. PATENT DOCUMENTS 3,618,829 A * 11/1971 Elmore ................. B05B 11/047
                                                222/320
4,559,038 A   12/1985 Berg et al.
5,954,485 A    9/1999 Johnson et al.
(Continued)

FOREIGN PATENT DOCUMENTS

WO   WO 2019/080544   5/2019
WO   WO 2020/018687   1/2020
(Continued)

*Primary Examiner* — Laura A Bouchelle
(74) *Attorney, Agent, or Firm* — Saliwanchik, Lloyd & Eisenschenk

(57) ABSTRACT

A cassette for attachment and use with an infusion pump apparatus. The cassette head having a low profile cassette head for attaching to the infusion pump apparatus and a flexible reservoir attached to the cassette head that can be filled with a fluid to be administered to a patient. The reservoir is enclosed in a flexible cover attached to the cassette. The flexibility of the cover and the reservoir inhibits the cassette head from disengaging from the infusion pump apparatus and allows the infusion pump apparatus to be primed by squeezing or pressing the cover and reservoir.

3 Claims, 7 Drawing Sheets

(56) References Cited

U.S. PATENT DOCUMENTS

| | | |
|---|---|---|
| 6,948,918 B2 | 9/2005 | Hansen |
| 7,018,375 B2 | 3/2006 | Berrigan |
| 7,351,226 B1 | 4/2008 | Herskowitz |
| 8,221,354 B2 | 7/2012 | Haase |
| 8,974,415 B2 * | 3/2015 | Robert .............. A61M 5/14228 |
| | | 604/151 |
| 9,629,955 B2 * | 4/2017 | Bresina ................ A61M 5/168 |
| 10,143,798 B2 | 12/2018 | Marbet et al. |
| 10,493,200 B2 | 12/2019 | Kim |
| 10,556,059 B2 | 2/2020 | Cross et al. |
| 10,918,571 B2 | 2/2021 | Juhnke et al. |
| 2005/0033233 A1 | 2/2005 | Kriesel |
| 2011/0152770 A1 | 6/2011 | DiPerna et al. |
| 2014/0194812 A1 | 7/2014 | Amirouche et al. |
| 2015/0250940 A1 | 9/2015 | Bresina et al. |
| 2016/0310662 A1 | 10/2016 | Schabbach et al. |
| 2017/0007767 A1 | 1/2017 | Schabbach et al. |
| 2018/0117244 A1 | 5/2018 | Jugl et al. |
| 2018/0214631 A1 | 8/2018 | Amirouche |
| 2018/0214636 A1 | 8/2018 | Amirouche |
| 2018/0221568 A1 | 8/2018 | He |
| 2018/0221571 A1 | 8/2018 | Carbone et al. |
| 2018/0272058 A1 | 9/2018 | Pizzochero et al. |
| 2019/0275216 A1 | 9/2019 | Leichner et al. |
| 2020/0023119 A1 | 1/2020 | Barnes et al. |
| 2020/0397981 A1 | 12/2020 | Hanson |

FOREIGN PATENT DOCUMENTS

| | | |
|---|---|---|
| WO | WO 2020/167542 | 8/2020 |
| WO | WO 2020/257439 | 12/2020 |
| WO | WO 2021/087249 | 5/2021 |
| WO | WO 2021/123995 | 6/2021 |

* cited by examiner

CASSETTE ASSEMBLY FOR AMBULATORY DRUG PUMP

CROSS-REFERENCE TO RELATED APPLICATIONS

This application is the U.S. National Stage Application of International Patent Application No. PCT/US2020/059913, filed on Nov. 11, 2020, which claims the benefit of U.S. Provisional Application Ser. No. 62/934,142, filed Nov. 12, 2019, the disclosures of which are hereby incorporated by reference in their entirety, including all figures, tables and amino acid or nucleic acid sequences.

BACKGROUND OF INVENTION

Infusion pumps are used to deliver a consistent and precise amount of a medically-prescribed fluid, such as a pharmaceutical or medicament, intravenously to a patient. Often referred to as "ambulatory devices," infusion pumps can deliver a consistent dose of a fluid to a patient at prescribed intervals while away from a medical facility. There are several types of infusion pumps, typically categorized by the operation of the pumping mechanism. They usually include a programmable control component with attached pump mechanism to control the flow of fluid to the patient. The programmable control component and pump apparatus are removably attached to a reservoir from which fluid is extracted by the pumping mechanism for intravenous delivery to the patient.

Peristaltic-type infusion pumps are commonly used to administer intravenous fluid chemotherapy drugs to a patient. The peristaltic pump mechanism is connected to the cassette, which has a rigid outer housing and an inner, negative-pressurized, flexible reservoir containing fluid. The negative-pressurization of the reservoir facilitates the peristaltic action of the infusion pump in drawing fluid into the intravenous line. The flexible reservoir collapses or contracts as fluid is drawn therefrom.

Many fluids, such as, for example, chemotherapy drugs, can be quite toxic and dangerous if contacted with the skin or inhaled. The rigid outer housing of a cassette facilitates connection of the cassette to the pump and also serves to protect the reservoir from punctures, leaks and other damage. If a leak does occur, the rigid outer housing can contain any spillage of the reservoir contents. Once the contents have been administered to the patient, the cassette can be disconnected and the inner reservoir removed and replaced. Alternatively, the entire cassette can be disposable.

The amount of fluid to be delivered to the patient in a given time can dictate the size of the cassette. A reservoir that contains a pharmaceutical or controlled substance is filled by a pharmacist or other authorized personnel. Cassettes are available in sizes with 50 ml, 100 ml, and 250 ml reservoirs. Hospitals and medical facilities routinely stock multiple sizes of cassettes and the associated IV infusion sets, which are usually obtained from different manufactures. This means the components are packaged separately and, unfortunately, often in mismatched quantities. Thus, it can be difficult for hospitals and medical facilities to stock equal numbers of cassettes and IV infusion sets.

After an infusion pump is filled, it often must be primed by drawing fluid from the reservoir into the intravenous lines to remove air within the reservoir and the line to establish a negative-pressure in the reservoir. This is usually accomplished with a syringe to pull air out and pull fluid into the line. This process is usually performed by the medical professional, usually a nurse, working directly with the patient. This can be a time-consuming process and cause some loss of the drug in the reservoir, which can be costly and possibly dangerous.

While considered an ambulatory device, the rigidity of the outer housing and the attached infusion pump requires patients to be cautious and often restricts patient mobility. The larger the cassette the more restrictions. If a patient sits, reclines, or otherwise applies pressure or force on the pump, the rigidity of the outer housing can cause torqueing or twisting of the cassette where it attaches to the infusion pump apparatus. If the cassette and pump are disengaged during use, the proper fluid dosage may not be delivered to the patient, reducing effectiveness and possibly causing serious health consequences. As such, most infusion pumps come equipped with safety features, such as alarms or other alerts that are activated in the event the infusion pump ceases normal operation. For example, if the reservoir or housing is unattached or insufficiently attached to the pump mechanism an alarm or other alert will be triggered. Once triggered, turning off the alarm or other alert often entails complete removal of the cassette and some manipulation (e.g., disassembly and subsequent reassembly) of the pump apparatus, which can be stressful for the patient. If, after reassembly, the alarm or alert is not turned off, the pump apparatus may have to be disassembled until the patient can obtain trained medical assistance to reset the pump apparatus. This can be particularly problematic when the alert sounds at night or when it is not possible to quickly obtain assistance.

BRIEF SUMMARY

The subject invention pertains to embodiments of an infusion cassette for attachment to an infusion pump apparatus for intravenous delivery of a fluid to a patient. The above-mentioned problems associated with the currently used cassettes with fully rigid outer housings for attachment to an infusion pump apparatus are solved by an improved cassette having a tough, flexible or pliable, non-rigid or semi-rigid outer cover containing a flexible or pliable inner fluid reservoir that securely contains a fluid under negative-pressure. The cover can be attached to a low-profile rigid cassette head that facilitates connection to the infusion pump apparatus. The flexible cover can inhibit disconnection of the cassette head from the pump mechanism by mitigating the effects of torqueing, twisting, pulling, or other critical forces that may be applied to the cover and inner reservoir. The non-rigid cover also allows fluid reservoir to be compressed or squeezed to force air out of and fluid into the tube, which eliminates the use of a syringe and can be more efficient in priming the pump mechanism. It can also allow fluid reservoir to be squeezed, pressed, massaged, or otherwise manipulated to minimize pockets of fluid that may be sealed off as the reservoir is evacuated or that otherwise might not be accessible for delivery to the patient.

The pump apparatus in conjunction with the negative-pressure fluid reservoir can facilitate extraction of all or most of the contents of the reservoir, minimizing residual or unused fluid in the reservoir. As fluid is removed, the flexible reservoir contracts or shrinks due to the negative-pressure, which can draw fluid towards the pump apparatus. Embodiments of the subject invention advantageously provide a single-size, negative-pressure reservoir, within the cover. Embodiments of a single-size reservoir are capable of containing any required amount of fluid and do not necessarily require that the reservoir be filled to capacity. The negative-pressure in the reservoir can facilitate movement of fluid towards the pump mechanism in the infusion pump and can minimize residual fluid in the reservoir. Thus, a single cassette can be used for any quantity of fluid and can eliminate the need for multiple sizes of fluid cassettes. The flexible, non-rigid cover is also more comfortable for the patient and, as fluid is administered, the reservoir and cover can become smaller and less bulky making the cassette increasingly more comfortable.

Additional flexibility and expansion capabilities can be incorporated into the cover by use of one or more extenders and/or expandable features. Extenders can provide additional flexion, particularly when used in the area where the rigid cassette head attaches to the cover. This can further inhibit disconnection of the cassette head from the pump apparatus by mitigating forces exerted against the cover. This can provide a patient with greater mobility, less stress, and fewer visits to a medical facility. Expandable features can provide flexion and additional volume to the container to accommodate the size of the internal reservoir.

It should be noted that this Brief Summary is provided to generally introduce the reader to one or more select concepts described below in the Detailed Disclosure in a simplified form. This Summary is not intended to identify key and/or required features of the claimed subject matter. Other aspects and further scope of applicability of the present invention will also become apparent from the detailed descriptions given herein. It should be understood, however, that the detailed descriptions, while indicating preferred embodiments of the invention, are given by way of illustration only, since various changes and modifications within the spirit and scope of the invention will become apparent from such descriptions. The invention is defined by the claims below.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which.

DETAILED DISCLOSURE

Figure 1:
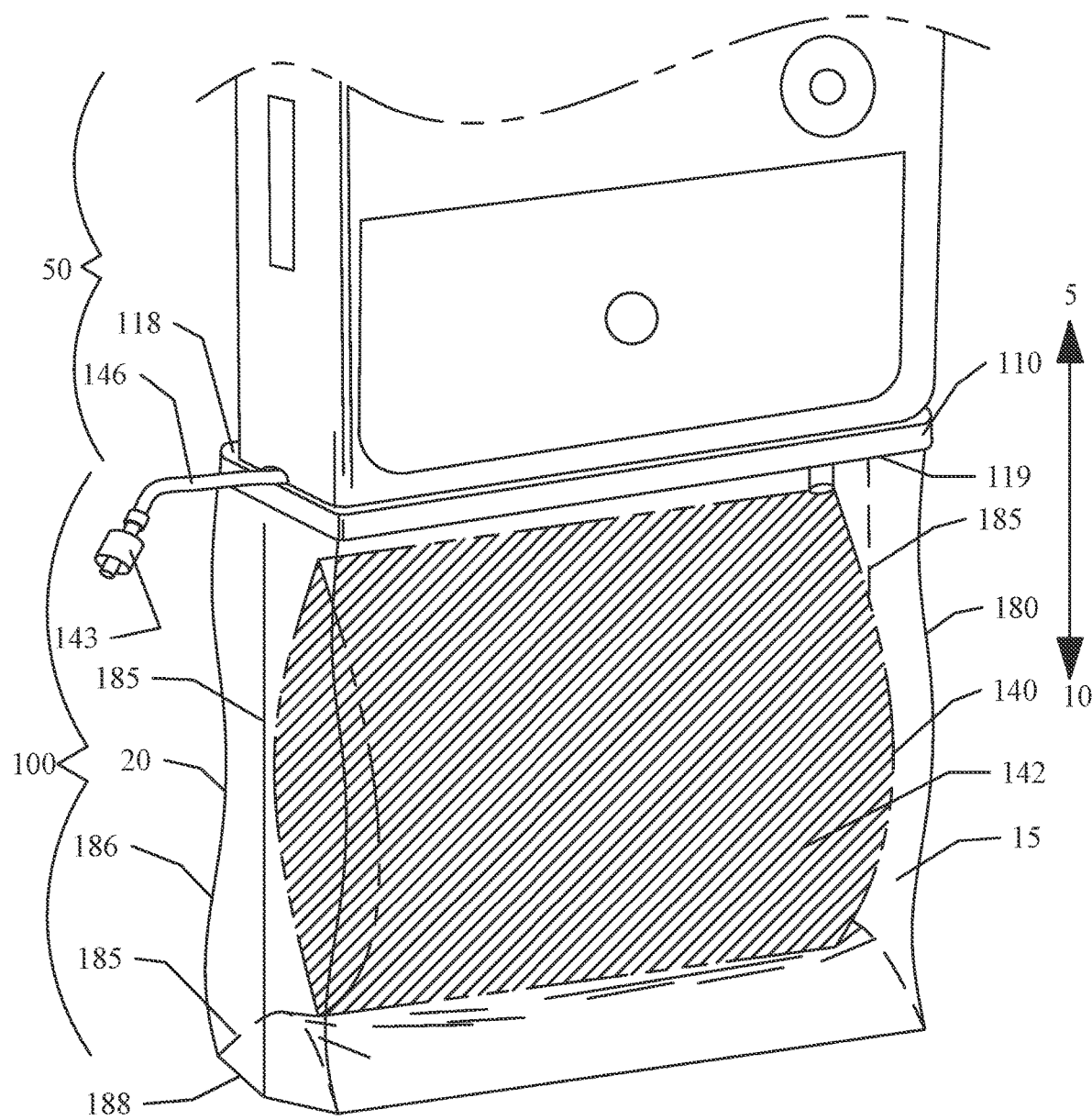
FIG. 1 is a perspective view of a cassette, according to an embodiment of the subject invention, shown attached to an infusion pump apparatus.

The subject invention pertains to improvements in intravenous delivery of a fluid to a patient with an infusion pump apparatus. More specifically, the subject invention provides one or more embodiments of an improved cassette for containing a negative-pressure reservoir that can be attached to an infusion pump apparatus. The improved cassette can provide a more pliable, less rigid outer cover and inner reservoir that is less restricted in how much it can contain, such that a single cassette can be utilized to contain a varying amount of fluid making it unnecessary to have multiple cassette sizes. The improved cassette can be more comfortable and less stressful for patients. The flexibility of the outer cover can improve patient mobility while using an infusion pump apparatus and can minimize the effects of forces exerted on the cassette caused by normal patient movements and activity. This can further reduce incidences of the cassette disconnecting from the pump and triggering an alarm or alert.

The following description will disclose that the subject invention is particularly useful in the field of intravenous drug infusion, specifically the use of infusion pump apparatuses. A person with skill in the art will be able to recognize numerous other uses that would be applicable to the devices and methods of the subject invention. While the subject application describes, and many of the terms herein relate to, a use for intravenous infusion, the invention is not limited to that use and other uses and obvious modifications therefore, apparent to a person with skill in the art and having benefit of the subject disclosure, are contemplated to be within the scope of the present invention.

In the description that follows, a number of terms are utilized. In order to provide a clear and consistent understanding of the specification and claims, including the scope to be given such terms, the following definitions are provided.

As used herein, the term "patient" refers to any vertebrate species, such as humans and animals and can range in age from neonates to elderly. Preferably, though not exclusively, the patient is of a mammalian species.

As used herein the term "critical force" refers to a magnitude of force capable of causing damage or otherwise interfering with the ability to operate. Specifically, it is a magnitude of force applied to an infusion pump apparatus and/or a cassette attached thereto that is capable of rendering an infusion pump apparatus inoperable or incapable of administering a fluid to a patient.

Further, as used herein, the term "fluid" refers to any ingredient, substance, drug, medicament, biomaterial, or combination thereof in liquid form capable of being administered intravenously to a patient.

The term "approximately" as used herein is defined as +/−5% in order to cover manufacturing variances and dosing tolerances.

Also, as used herein, and unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct, or indirect, physical or remote.

It is to be understood that the Figures and descriptions of embodiments of the present invention have been simplified to illustrate elements that are relevant for a clear understanding of the invention, while eliminating, for purposes of clarity, other elements that may be well known. Those of ordinary skill in the art will recognize that other elements may be desirable and/or required in order to implement the present invention. However, because such elements are well known in the art, and because they do not facilitate a better understanding of the present invention, a discussion of such elements is not provided herein. For example, the operation of peristaltic infusion pump apparatuses is known in the art and will not be described in detail here. Likewise, the IV infusion sets used to connect peristaltic infusion pump apparatuses to a patient are known in art and will not be described in detail here.

Finally, reference is made throughout the application to the "proximal end" or "proximal direction" and "distal end" or "distal direction." As used herein, the proximal end or proximal direction is that end or direction that approaches or is nearest to an infusion pump apparatus. For example, a cassette head is at the proximal end of the cassette for attachment to an infusion pump apparatus. Conversely, the distal end or distal direction is that end or direction that is furthest from an infusion pump apparatus when the cassette is attached thereto. For example, the inverted base of the cover can be at the distal end of the cassette.

Likewise, reference is made throughout the application to a "front" and a "back" of the subject invention. As used herein, the front refers to that side of fluid infusion pump and/or the cassette that is directed away from the body of a patient. Conversely, as used herein, the back refers to that side of fluid infusion pump and/or the cassette that is directed towards or in contact with the body of a patient.

The present invention is more particularly described in the following examples that are intended to be illustrative only because numerous modifications and variations therein will be apparent to those skilled in the art. As used in the specification and in the claims, the singular for "a," "an" and "the" include plural referents unless the context clearly dictates otherwise.

Reference will be made to the attached Figures on which the same reference numerals are used throughout to indicate the same or similar components. With reference to the attached Figures, which show certain embodiments of the subject invention, it can be seen in FIG. 1 that a cassette 100, of the subject invention, comprises a cassette head 110 at the proximal end 5 configured to be connectable to an infusion pump apparatus 50. A cassette includes a cover 180 operably attached and extending distal 10 to the cassette head to surround and enclose a fluid reservoir 140 that contains a fluid to be administered to a patient with the infusion pump apparatus. In one embodiment, the cover has expandable features 185 to accommodate different volumes of fluid in a reservoir. In one embodiment, the cover has an accordion-like extender 190 for additional flexibility. In a specific embodiment, the cover is operably connected to the cassette head by an accordion-like extender 190. Each of these general components can have one or more sub-components, which will be discussed in detail below.

There are several manufacturers of peristaltic infusion pump apparatuses 50 and cassettes. It will be appreciated that there can be variations in the configuration of the features of a cassette 100 of the subject invention, relative to the peristaltic infusion pump apparatus to which it is attachable. Nonetheless, there are certain features that are common to all or most of the cassettes utilized with peristaltic infusion pumps. A cassette 100, according to the subject invention is intended to be useful on any peristaltic infusion pump. As such, the components described herein with regard to a cassette head 110 can be arranged, configured, modified or otherwise made to perform with a prescribed peristaltic infusion pump.

Embodiments of a cassette 100 of subject invention utilize a cassette head 110 for operable attachment to an infusion pump apparatus 50, as shown, for example, in FIGS. 1, 3, and 6-9. A cassette head can be a rigid construct with a connecting surface 118 directed proximally 5 towards the infusion pump apparatus and a lower surface 119 directed distally towards the cover 180 and reservoir 140.

Figure 2:
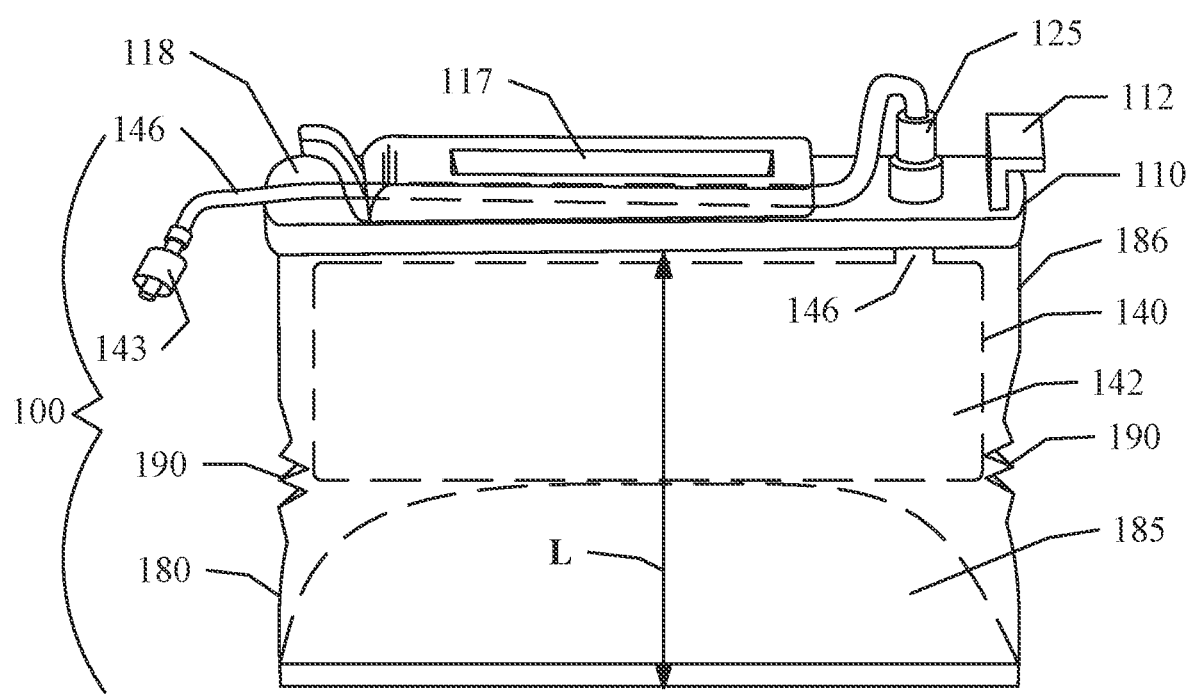
FIG. 2 is a front view of a cassette, according to an embodiment of the subject invention. As shown, the flexible cover and inner reservoir can have a variable length.

In one embodiment, a reservoir tube 146 extends from the reservoir and through a port 125 in the cassette head to extend across or through at least a portion of the cassette head 110, as shown, by way of example, in FIG. 2. A terminal end 143 of the reservoir tube can have a luer lock or other mechanism for attachment to the IV infusion set and ultimately to the patient. When the cassette head is in operable connection with the infusion pump apparatus 50, the rigidity of the cassette head can facilitate the peristaltic action of the infusion pump apparatus on the tube reservoir 146 to extract or draw fluid from the reservoir. In one embodiment, the cassette head 100 can have one or more guides 117 through which the pump apparatus contacts or engages with the reservoir tube 146, such as shown, for example, in FIGS. 2 and 4.

A cassette head 110 can also include one or more attachment components 112 that engage with and secure the cassette in operable attachment to the infusion pump apparatus 50. By way of non-limiting example, an attachment component can be an extension from the cassette head that connects or engages with an infusion pump apparatus, such as shown for example, in FIGS. 2 and 5. Alternatively, an attachment component can be aperture or opening in the cassette head to which the infusion pump apparatus attaches, such as shown, for example, in FIG. 5.

Figure 3:
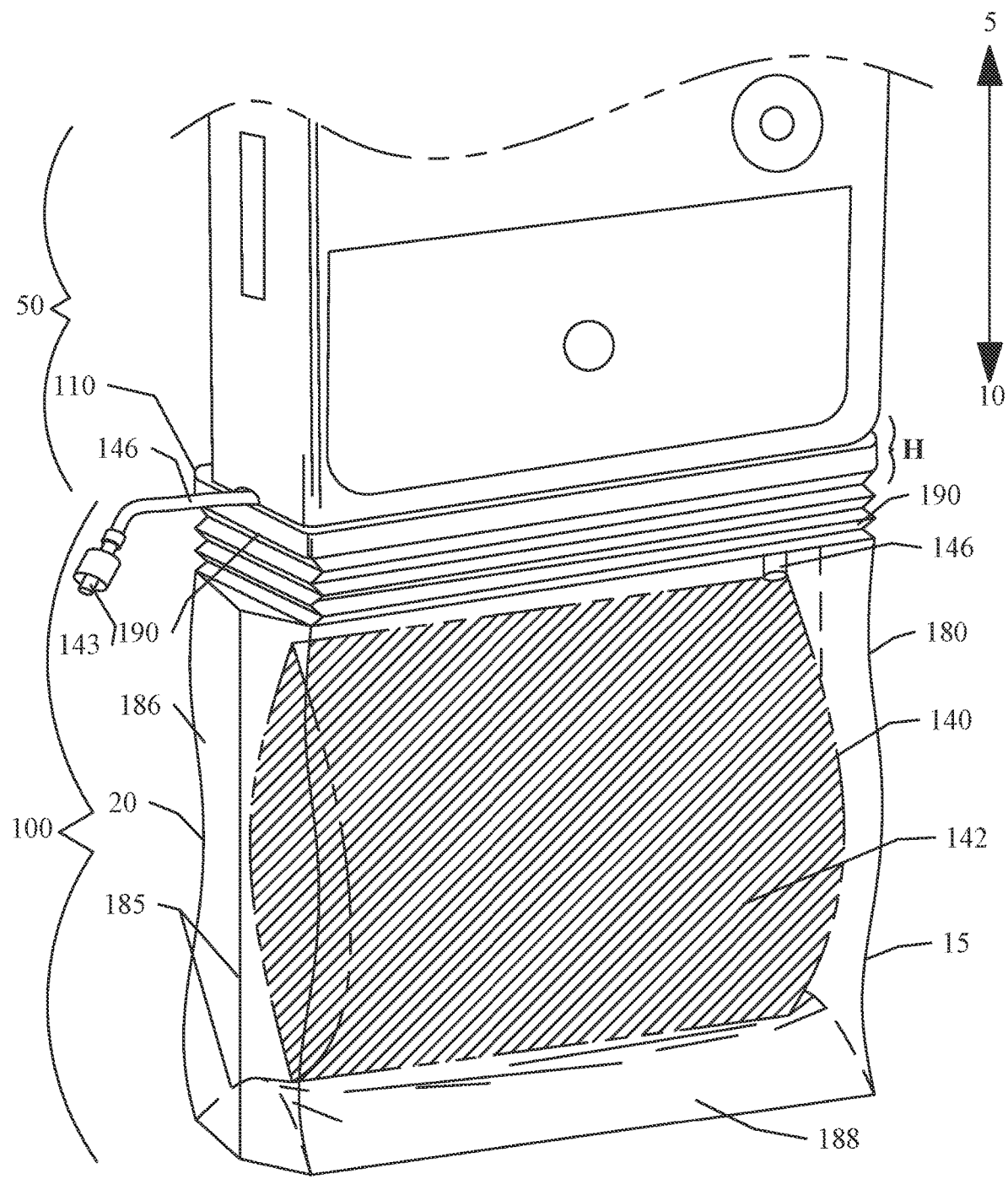
FIG. 3 is a perspective view of a cassette, according to an embodiment of the subject invention, which has an accordion-like extender to the cassette head, which is shown here attached to an infusion pump apparatus.

Preferably, embodiments of a cassette head 110 have a relatively low profile. In combination with a flexible cover, discussed below, a low profile can inhibit the application of critical forces on the cassette head. In one embodiment, the overall height (H), i.e., the distance between the connecting surface 18 and the lower surface 119 of the cassette head, as shown, for example, in FIG. 3, is less than the length (L) of the attached cover 180, as shown, for example, in FIG. 5. In one embodiment, the height H of a cassette is between approximately 0.25" and approximately 3". In another embodiment, the height H of a cassette is between approximately 0.5" and approximately 2.5". In a further embodiment, the height H of a cassette is between approximately 0.75" and approximately 2". In yet a further embodiment, the height H of a cassette is between approximately 0.5" and approximately 1.5".

A cassette head can be manufactured from any of a variety of materials. The material selected can depend upon several factors, such as, for example, whether the cassette 100 and/or the cassette head 110 will be reusable, disposable, capable of being sterilized and other factors known to those with skill in the art. Materials that can be suitable for a cassette head include, but are not limited to, polymeric materials (plastics), such as polycarbonate, polypropylene, acrylonitrile butadiene styrene (ABS), polyvinyl chloride, as well as metals, glass, ceramics, rubber, foam, or other materials, or some combination thereof. Ideally, the selected material will provide sufficient rigidity to ensure secure attachment to and operation of an infusion pump apparatus therewith.

Operably attached to the cassette head are a reservoir 140 and a cover 180, in which the reservoir is disposed. In one embodiment, at least one of the cover and reservoir are permanently attached to the cassette head 110, such that at least one is not intended to or cannot be removed without damaging the cassette head. Alternatively, at least one of the cover and reservoir can be removably attached, such that at least one is intended to and can be removed from and/or replaced without damaging the cassette head.

The reservoir of a typical known cassette can contain and, at least temporarily, store a fluid to be administered to the patient via an infusion pump apparatus 50. Typically reservoirs in cassettes are available in 50 ml, 100 ml, and 250 ml sizes. The amount of fluid to be administered is patient-specific. Thus, the size of the cassette selected can depend on the amount and type of fluid to be stored and administered from the internal reservoir. A smaller cassette, with a smaller reservoir, can be less inhibitive to patient mobility, but can also require more visits to the medical facility to replace the empty cassette. A larger cassette, with a larger reservoir, can reduce the number of visits to replace the cassette, but can be more restrictive to mobility. Hospitals usually store multiple sizes of reservoirs and the related IV infusion sets to accommodate patients' needs.

Advantageously, the reservoir embodiments of the subject invention can accommodate larger volumes, to reduce medical visits, without inhibiting and even improving patient mobility. Embodiments of the subject invention provide a single size reservoir 140 with a container portion 142 capable of containing and, at least temporarily, storing a maximum amount of fluid to be administered to a patient via an infusion pump apparatus 50. In one embodiment, a reservoir container portion has a maximum volume of between approximately 250 ml and 300 ml. Thus, a reservoir of the subject invention can contain and store any volume of fluid up to and including the maximum volume. By way of example, embodiments of a single-size reservoir of the subject invention can contain and, at least temporarily, store fluid volume of at least 50 ml, 75 ml, 100 ml, 125 ml, 150 ml, 175 ml, 200 ml, 225 ml, 250 ml, 275 ml, and 300 ml or a volume in a range between any two of the listed values. Thus, an embodiment of a single size reservoir can accommodate various fluid volumes, thereby minimizing the number patient visits seeking medical assistance in replacing a cartridge.

In a further embodiment, a reservoir 140 has a tube 146 attached at the proximal end 5 of the container portion 142 through which fluid is drawn out of the reservoir, as discussed above. A terminal end 143 of the tube can extend through a port 125 in the cassette head 110 and have a luer lock or other connecting mechanism 148 for attaching the IV infusion set that attaches to the patient. For an infusion pump apparatus 50 to operate, the reservoir has a negative internal pressure. This allows the peristaltic action of the infusion pump apparatus to act on the tube to draw fluid from the reservoir. This mode of operation is known in the art and employed with a variety of infusion pump apparatuses. Ideally, embodiments of a single size reservoir and the associated tube can be utilized with known infusion pump apparatuses.

Figure 4:
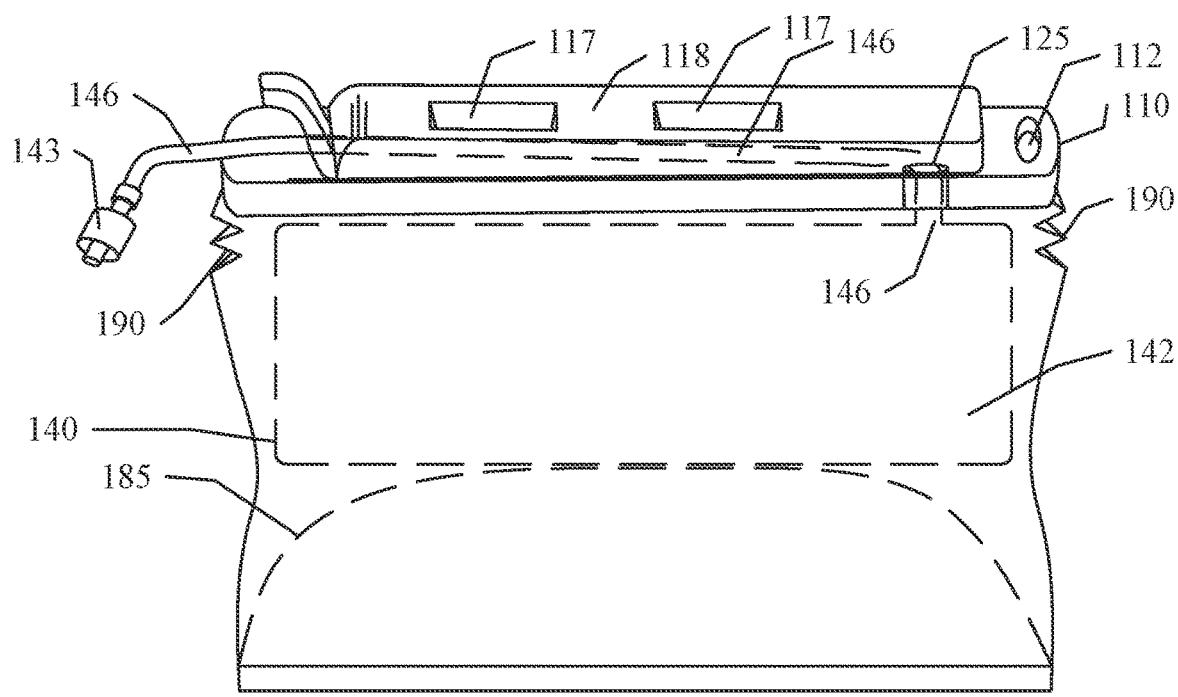
FIG. 4 is a front view of a cassette, according to an embodiment of the subject invention, with an accordion-like extender between the attachment head and the flexible cover. The outer cover is shown with an inverted base expandable feature that allows for expansion of the cover length to accommodate a greater quantity of fluid in the reservoir. The reservoir shown here does not contain a sufficient quantity of fluid to require expansion of the base to increase volume of the outer cover.
Figure 5:
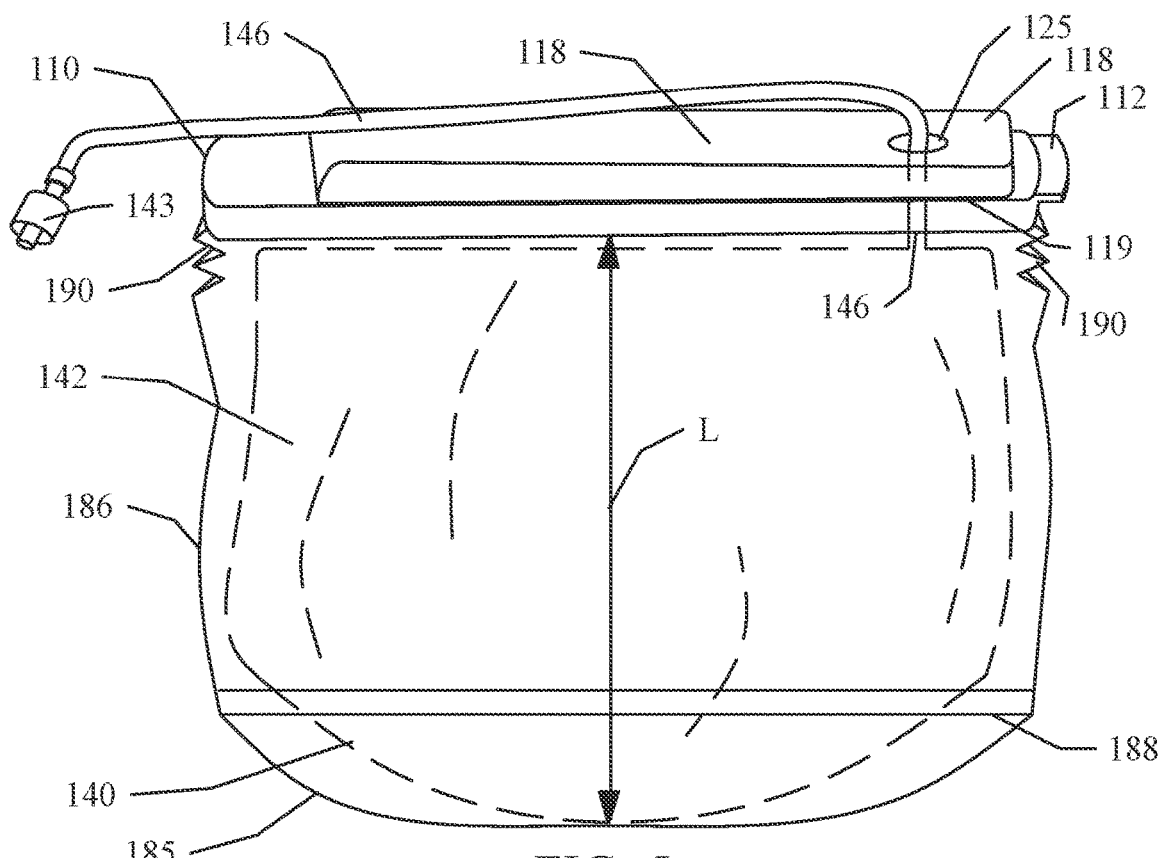
FIG. 5 is a front elevation view of a fluid cassette, according to an embodiment of the subject invention, with an accordion-like extender between the cassette head and the flexible cover. The outer cover is shown with an inverted base expandable feature that allows for expansion of the cover length to accommodate a greater amount of fluid in fluid reservoir. The reservoir shown here has a sufficient quantity of fluid therein to push the inverted base downward, increasing the volume of the outer cover.

A reservoir can contain any of a variety of fluids. Preferably, a reservoir comprises a biocompatible material that is non-reactive, so that any fluid therein does not react with the reservoir material. Such materials can include various polymeric films, such as, but not limited to polyethylene, polypropylene, polyvinyl chloride, Ethylene-Vinyl Acetate (EVA), other materials known in the art and combinations thereof. In one embodiment, the reservoir comprises an elastic material that flexible and/or expands when filled with fluid. FIGS. 4 and 5 illustrate examples of an elastic reservoir that shrinks or collapses as fluid is extracted.

A cover 180 can surround and protect a reservoir 140. Further, a cover can be puncture and leak proof and provide a sealed enclosure around a reservoir. In one embodiment, a cover is flexible, pliable, foldable, bendable, or otherwise capable of adjusting, modifying, or changing shape. In a further embodiment, a cover can comprise a material that is the same or similar to that of a reservoir, as described above. Alternatively, a cover can comprise one or more different materials, such as, for example, nylon, natural or synthetic rubber, polyvinyl chloride, synthetic elastomers, Kevlar®, Ethylene-Vinyl Acetate (EVA), Thermoplastic Polyurethane (TPU), or like materials, other similarly tough suitable materials, and combinations thereof. In a further embodiment, a cover comprises two or more layers of the same or different materials.

The flexibility of the cover provides the advantageous ability to squeeze or compress the reservoir 140 therein. This allows the reservoir to be primed by squeezing or pressing to force fluid into the reservoir tube 146, thereby removing air within the reservoir and tube 146 to which the IV infusion set is attached. Further, the reservoir can be pressed or massaged or otherwise manipulated as fluid is drawn out to inhibit the formation of sealed off pockets of fluid that can form as the reservoir collapses or shrinks. The one or more materials chosen for a cover can facilitate these processes. In a further embodiment, the one or more materials or some portion thereof can be transparent, so that the reservoir can be observed.

It is not uncommon for patients to hit, bump, press, jostle, bend, or make other types of contact with the infusion pump apparatus. With a rigid cover cassette such contact can disrupt the operation of the infusion pump, which can activate alarms or other alerts that the infusion pump apparatus is no longer working correctly. In other words, the magnitude of critical force necessary to disrupt an infusion pump apparatus by contact can be lower with a rigid cassette, such that minimal contact can be disruptive. Such disruption can be stressful to the patient and require considerable effort and time to correct.

The embodiments of a cover 100 of the subject invention are more advantageous in reducing these types of interruptions because the pliability of materials raises the magnitude of critical force necessary to disrupt or disconnect the cassette head. The pliable cover is able to absorb, redirect, or otherwise mitigate certain forces, thereby raising the magnitude of critical force capable of disrupting the infusion pump apparatus. This means that normal or even some above-normal or excessive contact with the cover can be inhibited from interfering with the operation of the infusion pump apparatus.

To further increase the level of critical force necessary to disconnect the cassette head 100 or interfere with the operation of the infusion pump apparatus, the cover can have one or more extenders 190. An extender can comprise one or a plurality of pleats, accordion-like folds, or fan-folds arranged horizontally or substantially parallel to the cassette head, such that all or some portion of the cover can be extended and retracted in a proximal 5 to distal 10 direction. An accordion-like extender can be located anywhere on a cover. FIG. 2 illustrates an example of an extender on a cover. FIGS. 3, 4, and 5 illustrate embodiments having an extender located between the cassette head 100 and the cover. The use of an extender can reduce the effect of pulling forces exerted on the cover in a direction that pulls the cover away from the cassette head and can increase the level of critical forces necessary to disconnect the cassette head from an infusion pump apparatus. Ideally, the extender will inhibit the normal activities of the patient from disconnecting the cassette head from the pump.

The cover embodiments of the subject invention can accommodate a reservoir of variable size and volume. As discussed above, a cover can advantageously accommodate a reservoir capable of containing any amount of fluid up to approximately 300 ml. Ideally, as fluid is administered, the cover can shrink, contract, or otherwise reduce in size, so as to accommodate the likewise reduction in the reservoir size and/or volume. In one embodiment, the one or more materials of the cover can have elastomeric qualities that allow the cover, or some area thereof, to be stretched to accommodate larger volumes of fluid in the reservoir. As the reservoir is depleted and shrinks in size and/or volume accordingly, the cover can likewise shrink to accommodate the changing size and/or volume of the reservoir.

Figure 9:
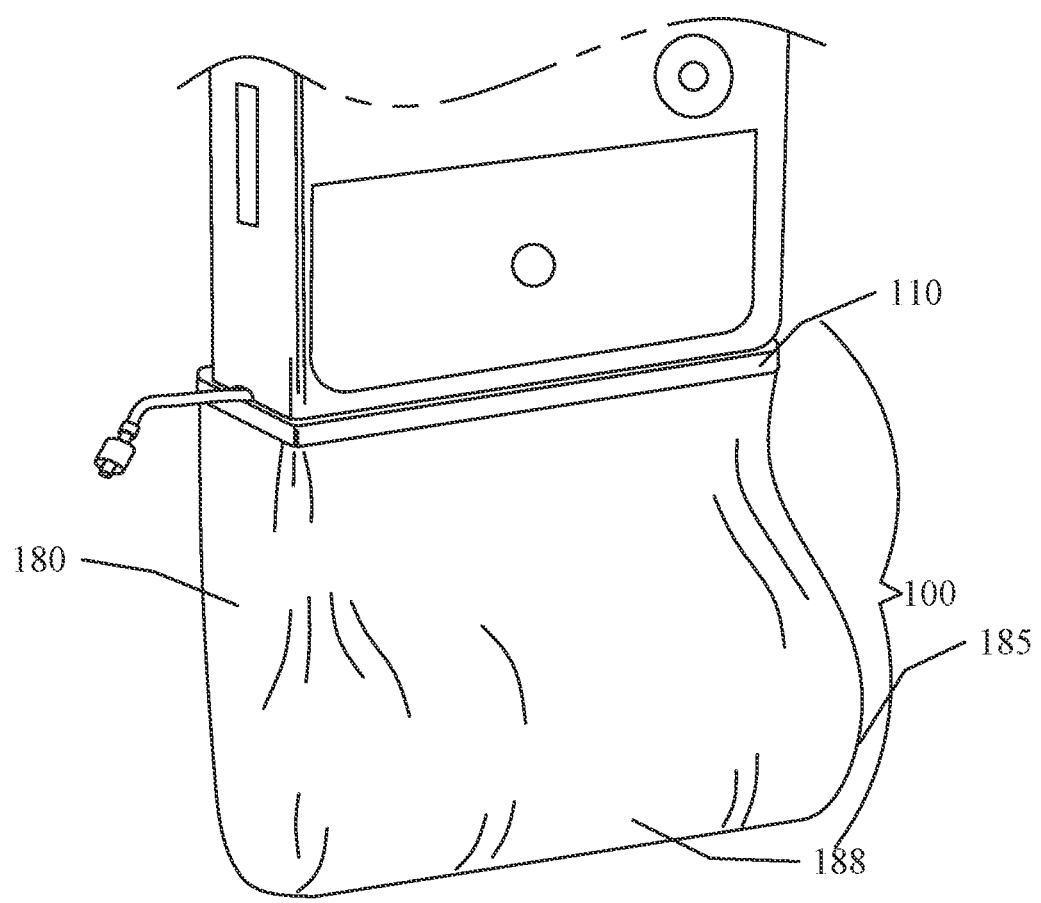
FIG. 9 is a perspective view of an alternative embodiment of a fluid cassette, according to the subject invention, having a cover with an enlarged or protuberant bottom portion to accommodate enlargement of the internal reservoir.

In one embodiment, a cover 180, or some portion thereof, can be formed from an elastomeric, flexible, or pliable material that readily accommodates modification of the shape. In some embodiments, certain portions of the cover have enlarged or expanded area that facilitate expansion of the reservoir into those areas. Likewise, certain portions of the cover can be constricted, narrowed, or otherwise reduced in size or volume to direct fluid in a reservoir to other areas. FIG. 9 illustrates an embodiment of a cover with a waveform shape that defines a protuberant or enlarged distal end 10 in which the reservoir can expand.

Alternatively, the cover 180 can be configured with one or more expandable features 185 that allow the cover to expand and contract or otherwise adjust in size or be modified to accommodate the changing volume in the reservoir. Expandable features can include, but are not limited to, pleats, folds, gussets, fan-folds, overlaps, bendable areas, pop-out sections, and other structural configurations that allow at least one of the front 15, back 20, bottom end 188, and/or one or more sides 186 of the cover to be expanded and/or reduced in size. FIGS. 1 and 3 illustrate examples of a cover with an expandable feature in the form of a fold or pleat on each side 186 that allow the sides of the cover to be unfolded to enlarge or bulge outward and to be refolded to make the cover smaller.

Figure 6:
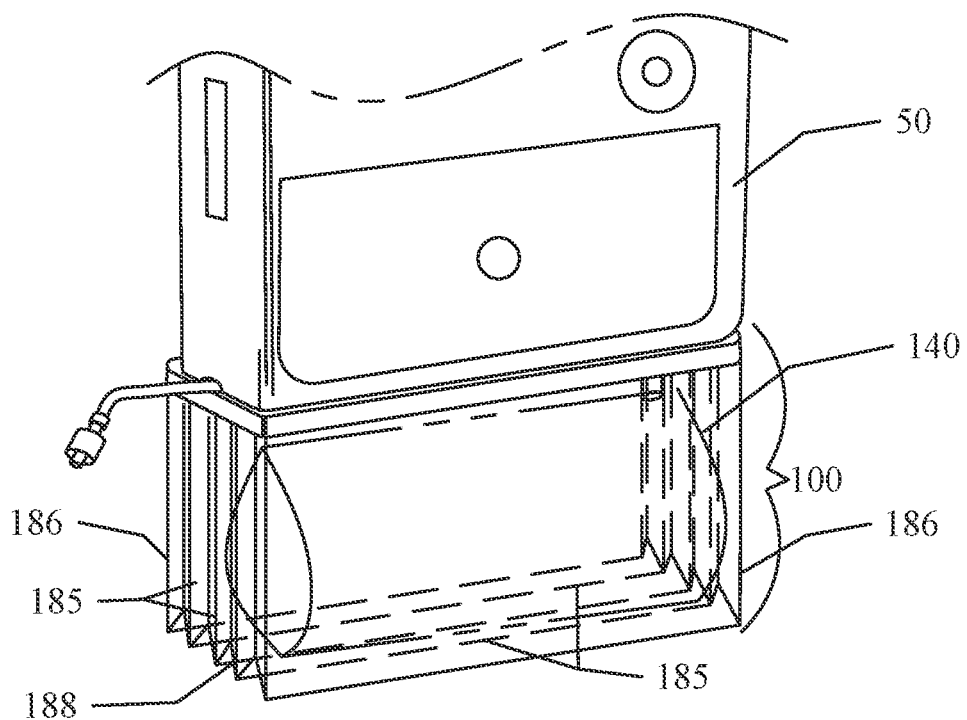
FIG. 6 is perspective view of an embodiment of a fluid cassette, according to the subject invention, operably attached to an infusion pump apparatus. This embodiment includes expandable features in the form of a plurality of fan-fold pleats in the cover that allow for expansion.
Figure 7:
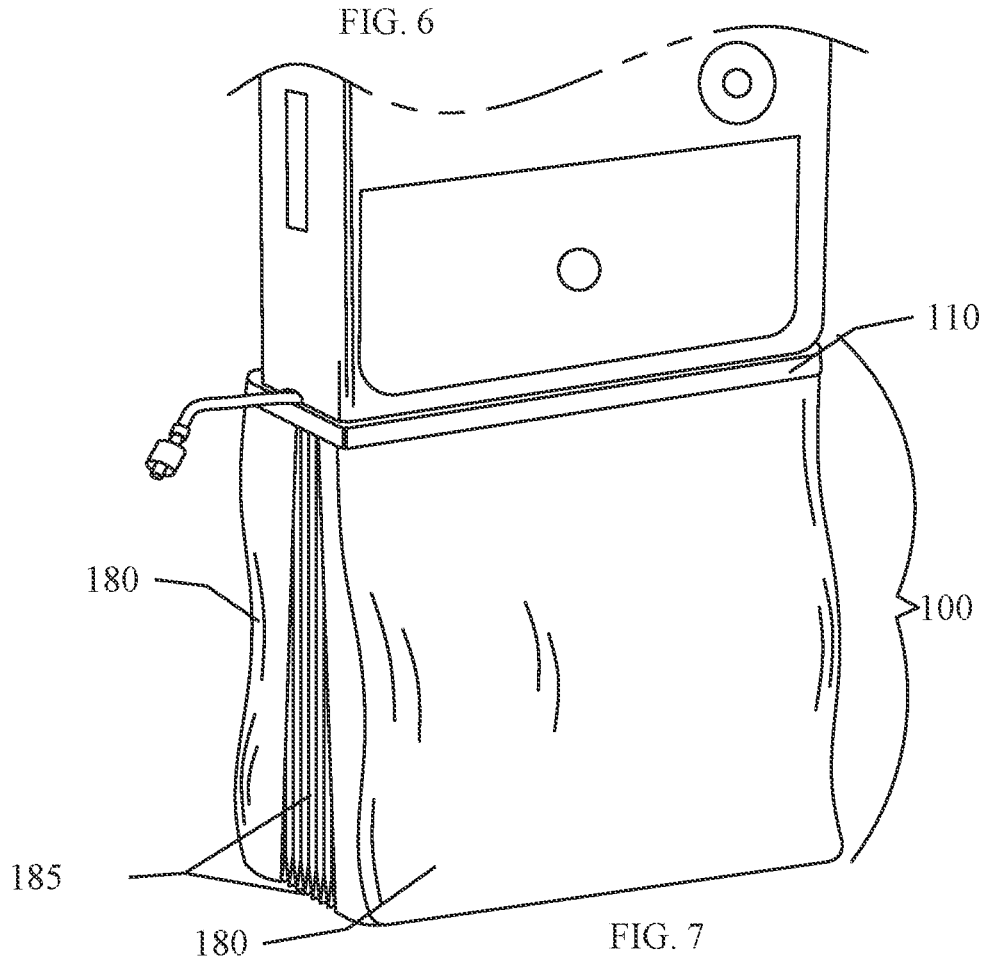
FIG. 7 is perspective view of an embodiment of a fluid cassette, according to the subject invention, operably attached to an infusion pump apparatus. This embodiment illustrates a cover having multiple pleats incorporated along the sides to allow front-to-back expansion near the distal end and between the front side and back side of the cover.

In some instances the cover 180 may require minimal or no expansion to accommodate the reservoir. In other instances, the cover may require maximal expansion to accommodate a reservoir and fluid. For example, a cover can have expandable features 185 in the form of multiple, two or more, fan-folded pleats. The multiple pleats can provide a cover with variable expansion capabilities. FIG. 6 illustrates a cover with multiple pleats arranged along each of the sides 186 and bottom side 188, so as to provide approximately equal expansion along the sides and bottom of the cover. FIG. 7 illustrates an alternative embodiment of a cover with multiple pleats that taper towards the proximal end 5 of the cover, so that the cover can expand more at the distal end 10. More specifically, the multiple tapered pleats can allow for the distal end of the cover to expand in a front-to-back direction. In a further embodiment, the flexibility of the cover as well as the use of the multiple pleats can allow the cover to expand to approximately 1.5 times the fully compressed or unexpanded size.

In some instances it can be beneficial for a cover 180 to be expandable, while at least partially maintaining an overall shape or configuration. Expandable features can be incorporated that allow for expansion of a cover, but still retain an overall outward shape of the cover. In one embodiment, a cover has one or more pleats or folds incorporated into the sides 186 between the front side 15 and the back side 20 that allow the cover to expand and retract in a front to back direction, but the overall shape of the front and back are maintained. The front and back can still have some flexibility. FIG. 7 illustrates one non-limiting example of this embodiment, where a plurality of pleats or folds is incorporated between the front side and the back side of a flexible or semi-flexible cover. It can be seen that the cover in this embodiment is capable of expanding, while still at least partially maintaining the overall outward shape or configuration of the cover. Thus, when a reservoir 140 is filled so that it causes expansion of the cover the expandable features will bulge, open, or otherwise expand to modify the cover and provide the necessary size and/or volume to accommodate the reservoir. As fluid in the reservoir is depleted, the expandable features will retract, close, or otherwise reduce the size or volume of the cover until fully retracted to the original shape.

Figure 8:
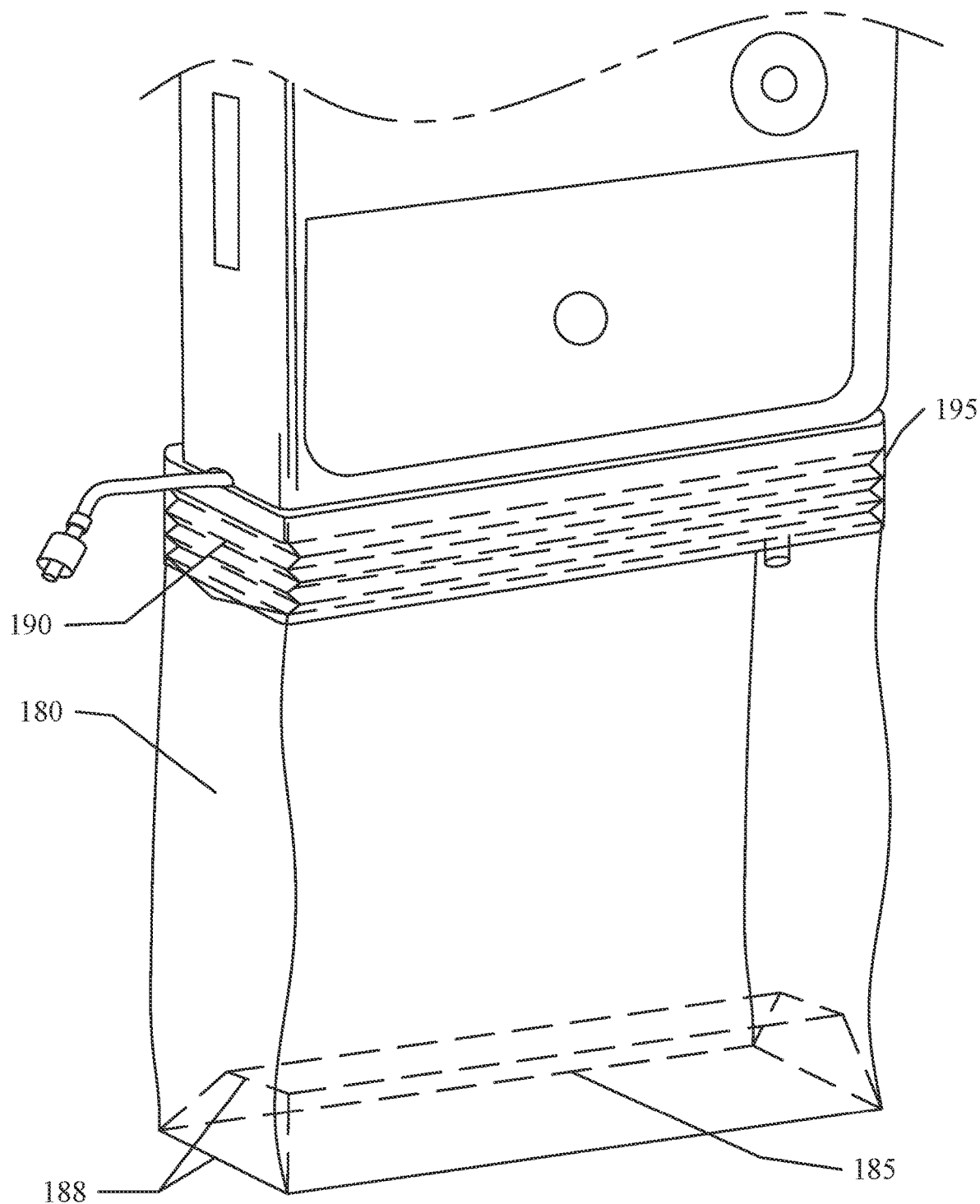
FIG. 8 is a perspective view of an embodiment of a fluid cassette, according to the subject invention, having an according-like extender that connects the cover to the cassette head, such as shown, for example, in FIG. 3. This embodiment includes a sheath that extends distally from the cover and over the accordion-like extender. Also shown is an embodiment of a "pop-down" bottom side expandable feature that provides expansion of the cover length.

In a further embodiment, the distal end 5 of a cover 180 can have an inverted base where expandable features 185 allow the bottom side 188 to expand and contract or fold into and out of the cover. In one embodiment, the bottom side 188 has an expandable feature that can be tucked in or inverted into the bottom side, but can bulge or be pushed outward, as necessary, thereby gradually or incrementally increasing the length (L) of a cover to accommodate a fuller reservoir. FIG. 4 illustrates a non-limiting example of a cover where the bottom side 188 has an expandable feature 185 that creates an inverted base. FIG. 5 shows how the inverted expandable feature can bulge or expand out to extend below the sides 186 increasing the length L of the cover and providing additional space for a fuller reservoir. FIG. 8 illustrates an alternative embodiment of an expandable feature 185 comprising a "pop-out" portion or more rigid or semi-rigid inverted bottom side 188 expandable feature that can extend the bottom side of the cover. In this embodiment, the expandable feature can be fully extended or fully retracted to increase or decrease the length of the cover.

Infusion pump apparatuses are used for a administering a variety of fluids and drugs to patients. Many of the drugs administered with an infusion pump apparatus, such as chemotherapeutic drugs, are most effective when administered in precise dosages over an extended period of time. Interruption during the administration period can be dangerous or have deleterious effects on the patient. Most of the time, such disruptions are caused by disconnection of the cassette that attaches to the pump mechanism and that holds fluid or drug. The embodiments of the subject invention provide an improvement to the cassettes used with infusion pump apparatuses. The improved cassettes can make it more difficult to disconnect the cassette during normal activity and can be more comfortable for the patient.

The scope of the invention is not limited by the specific examples and suggested procedures and uses related herein since modifications can be made within such scope from the information provided by this specification to those skilled in the art.

EXEMPLARY EMBODIMENTS

Embodiment 1: A cassette, configured to be attached to an infusion pump apparatus, comprising:
  a cassette head comprising,
  a port; and
  an attachment component for attaching to the infusion pump apparatus;
  a flexible reservoir, attached to the cassette head, comprising,
  a tube that engages with the port and a terminal end, adapted to be attached to an IV infusion set; and,
  a flexible cover, attached to the cassette, enclosing the reservoir.

Embodiment 2: The cassette according to embodiment 1, further comprising an expandable feature on the cover.

Embodiment 3: The cassette according to embodiment 2, wherein the expandable feature is a pleat, fold, gusset, bendable-area, or elastic portion where the shape of the cover is modifiable to accommodate expansion or contraction of the reservoir therein.

Embodiment 4: The cassette according to embodiment 3, comprising the expandable feature on a bottom side of the cover to increase a length of the cover.

Embodiment 5: The cassette according to embodiment 2, wherein the expandable feature comprises an extender.

Embodiment 6: The cassette according to embodiment 5, wherein the extender comprises one or more accordion-like folds.

Embodiment 7: The cassette according to embodiment 5, wherein the extender is between the cover and the cassette head.

Embodiment 8: The cassette according to embodiment 3, wherein the expandable feature forms one or more sides of the cover.

Embodiment 9: The cassette according to embodiment 3, wherein the expandable feature forms part of a side between a front side and a back side of the cover.

Embodiment 10: The cassette according to embodiment 1, further comprising a guide on the cassette head that engages with the infusion pump.

Embodiment 11: The cassette according to embodiment 1, wherein the cassette head has a height between approximately 0.5" and approximately 2.5".

Embodiment 12: The cassette according to embodiment 10, wherein the cassette head has a height between approximately 0.75" and approximately 2".

Embodiment 13: The cassette according to embodiment 11, wherein the cassette head has a height between approximately 0.5" and approximately 1.5".

Embodiment 14: A method for administering a fluid to a patient utilizing an infusion pump apparatus comprising:
obtaining a cassette comprising,
  a cassette head comprising,
  a port; and
  an attachment component for attaching to the infusion pump apparatus;
  a flexible reservoir attached to the cassette head comprising,
  a tube that engages with the port and has a terminal end, adapted to be attached to an IV infusion set for intravenously administering fluids to a patient; and
  a flexible cover attached to the cassette and enclosing the reservoir;
  attaching the cassette to the infusion pump apparatus; and
  attaching to the tube and IV infusion set;
such that, when the infusion pump apparatus is activated, fluid is drawn by the infusion pump apparatus from the reservoir into the tube and the IV infusion set.

Embodiment 15: The method according to embodiment 14, further comprising squeezing the cover and reservoir to prime the tube and IV infusion set.

Embodiment 16: The method according to embodiment 14, further comprising pressing or squeezing the cover and reservoir to inhibit or remove sealed-off pockets of fluid in the reservoir.

Embodiment 17: The method according to embodiment 14, wherein the cover comprises an expandable feature.

Embodiment 18: The method according to embodiment 17, wherein the expandable feature is a pleat, fold, gusset, bendable-area, or elastic area where the shape of the cover is modifiable to accommodate expansion of the reservoir therein.

Embodiment 19: The method according to embodiment 18, wherein the expandable feature is on a bottom side of the cover that bulges outward from the cover to increase a length of the cover.

Embodiment 20: The method according to embodiment 17, wherein the expandable feature comprises an extender.

Embodiment 21: The method according to embodiment 20, wherein the extender is between the cover and the cassette head.

Embodiment 22: The method according to embodiment 21, wherein the extender comprises one or more accordion-like folds.

Embodiment 23: The method according to embodiment 18, wherein the expandable feature forms one or more sides of a cover.

Embodiment 24: The method according to embodiment 23, wherein the expandable features is between a front side and a back side of the cover.

Embodiment 25: The method according to embodiment 14, wherein the cassette head further comprises a guide that engages with the infusion pump.

Embodiment 26: The method according to embodiment 14, wherein the cassette head has a height between approximately 0.5" and approximately 2.5".

Embodiment 27: The method according to embodiment 26, wherein the cassette head has a height between approximately 0.75" and approximately 2".

Embodiment 28: The method according to embodiment 27, wherein the cassette head has a height between approximately 0.5" and approximately 1.5".

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

I claim:

1. A cassette, configured to be attached to an infusion pump apparatus, comprising:
   a cassette head comprising,
      a port;
      an attachment component for attaching to the infusion pump apparatus;
   a flexible reservoir, attached to the cassette head, comprising,
      a tube that engages with the port and a terminal end, adapted to be attached to an IV infusion set;
   a flexible cover, attached to the cassette, enclosing the reservoir; and
   an extender between the cover and the cassette head.

2. A method for administering a fluid to a patient utilizing an infusion pump apparatus comprising:
   obtaining a cassette comprising,
      a cassette head comprising,
         a port; and
         an attachment component for attaching to the infusion pump apparatus;
      a flexible reservoir attached to the cassette head comprising,
         a tube that engages with the port and has a terminal end, adapted to be attached to an IV infusion set for intravenously administering fluids to a patient;
      a flexible cover attached to the cassette and enclosing the reservoir;
      an extender between the cover and the cassette head;
   attaching the cassette to the infusion pump apparatus; and
   attaching to the tube and IV infusion set;
such that, when the infusion pump apparatus is activated, fluid is drawn by the infusion pump apparatus from the reservoir into the tube and the IV infusion set.

3. A method for administering a fluid to a patient utilizing an infusion pump apparatus comprising:
   obtaining a cassette comprising,
      a cassette head comprising,
         a port; and
         an attachment component for attaching to the infusion pump apparatus;
      a flexible reservoir attached to the cassette head comprising,
         a tube that engages with the port and has a terminal end, adapted to be attached to an IV infusion set for intravenously administering fluids to a patient;
      a flexible cover attached to the cassette and enclosing the reservoir;
      one or more accordion-like folds between the cover and the cassette head;
   attaching the cassette to the infusion pump apparatus; and
   attaching to the tube and IV infusion set;
such that, when the infusion pump apparatus is activated, fluid is drawn by the infusion pump apparatus from the reservoir into the tube and the IV infusion set.

* * * * *